United States Patent [19]

Arnold, Jr.

[11] Patent Number: 5,539,097
[45] Date of Patent: Jul. 23, 1996

[54] OLIGONUCLEOTIDE POLYMERIC SUPPORT SYSTEM

[75] Inventor: Lyle J. Arnold, Jr., San Diego, Calif.

[73] Assignee: Molecular Biosystems, Inc., San Diego, Calif.

[21] Appl. No.: 272,290

[22] Filed: Jul. 8, 1994

Related U.S. Application Data

[63] Continuation of Ser. No. 492,418, Mar. 6, 1990, abandoned, which is a continuation of Ser. No. 97,298, Sep. 14, 1987, abandoned, which is a continuation of Ser. No. 664,981, Oct. 6, 1984, abandoned, which is a continuation-in-part of Ser. No. 528,856, Sep. 2, 1983, abandoned.

[51] Int. Cl.$^6$ .................... C07H 19/067; C07H 19/167; C07H 21/02
[52] U.S. Cl. .................... 536/25.3; 536/24.3; 435/6
[58] Field of Search .................... 536/25.3, 25.31, 536/25.4

[56] References Cited

U.S. PATENT DOCUMENTS

| | | | |
|---|---|---|---|
| 3,440,190 | 4/1969 | Melby | 536/54.3 |
| 3,488,405 | 1/1970 | Trementozzi et al. | 525/79 |
| 3,520,839 | 7/1970 | Milligan et al. | 525/404 |
| 3,832,423 | 8/1974 | Milkovich et al. | 525/286 |
| 3,850,749 | 11/1974 | Kaufmann et al. | 435/91 |
| 3,887,653 | 6/1975 | Konishi et al. | 525/301 |
| 3,898,301 | 8/1975 | Konishi et al. | 525/77 |
| 4,085,168 | 4/1978 | Milkovich et al. | 525/59 |
| 4,373,071 | 2/1983 | Itakura | 525/375 |
| 4,401,796 | 9/1983 | Itakura | 525/340 |
| 4,458,066 | 7/1984 | Caruthers et al. | 536/25.34 |
| 4,500,707 | 2/1985 | Caruthers et al. | 536/25.34 |

FOREIGN PATENT DOCUMENTS

| | | |
|---|---|---|
| 0035719 | 2/1981 | European Pat. Off. |
| 0079139 | 10/1982 | European Pat. Off. |
| 2125798 | 3/1984 | United Kingdom |
| 8203079 | 9/1982 | WIPO |

OTHER PUBLICATIONS

Matteucci et al, "Synthesis of Deoxynucleotides on a Polymer Support," *J. Am. Chem. Soc.*, 103(11), 3185–3191 (1981).

Sommer et al., "Chemische Syntheses von Desoxyoligonucleotiden mit 5'-Phosphatgruppe am Polymeren Träger," *Chem. Ber.*, 107, 24–33 (1974).

Koster (I), "Polymer Support Oligonucleotide Synthesis VI. Use of Inorganic Carriers," *Tetrahedron Letters*, 1972, (16), 1527–1530.

Koster (II), "Polymer Support Oligonucleotide Synthesis VII. Use of Sephadex LH 20," *Tetrahedron Letters*, 1972, (16), 1531–1534.

Koster (III), "Die Bedeutung der Chemischen Synthesis von DNA für die Gentechnologie," *Arzneim.-Forsch/Drug Res.*, 30, 548–557 (1980).

Matteucci et al. (II), "The Synthesis of Oligodeoxypyridines on a Polymer Support," *Tetrahedron Letters*, 21, 719–722 (1980).

Arshady et al., "Easily Prepared Polar Support for Solid Phase Peptide and Oligonucleotide Synthesis. Preparation of Substance P and a Nonadeoxyribonucleotide," *J. Chem. Soc. Chem. Comm.*, 1979, 423–425.

Dunn et al., "Mapping Viral mRNAs by Sandwich Hybridization," *Methods in Enzymology*, 65, 468–478 (1980).

Ranki et al., "Sandwich Hybridization as a Convenient Method for the Detection of Nucleic Acids in Crude Samples," *Gene*, 21, 77–85 (1983).

Palva et al., "ompA Gene in the Detection of *Escherichia coli* and Other Enterobacteriaceae by Nucleic Acid Sandwich Hybridization," *J. Clin. Microbiol.*, 18, 92–100 (1983).

Bunemann, "Immobilization of Detatured DNA to Microporous Supports: II. Steric and Kinetic Parameters of Heterogeneous Hybridization Reactions," *Nucleic Acids Research*, 10, 7181–7196 (1982).

Hayakawa et al., "The Allylic Potection Method in Solid-Phase Oligonucleotide Synthesis. An Efficient Preparation of Solid-Anchored DNA Oligomers," *J. Am Chem. Soc.*, 112, 1691–1696 (1990).

Chow et al., "A High Capacity, Reusable Oligodeoxythymidine Affinity Column," *Analytical Biochemistry*, 175, 63–66 (1988).

Blanks et al., "An Oligonucleotide Affinity Column for the Isolation of Sequence Specific DNA Binding Proteins," *Nucleic Acids Research*, 16(21), 10283–10298 (1988).

(List continued on next page.)

*Primary Examiner*—Douglas W. Robinson
*Assistant Examiner*—L. Eric Crane
*Attorney, Agent, or Firm*—Fish & Richardson

[57] ABSTRACT

A versatile polymeric support system for the synthesis of oligonucleotides is provided featuring a universal primer which allows chain elongation, in either the 3' or 5' direction, with any currently available DNA or RNA synthesis method, by a process which utilizes oxidatively cleaved primers to facilitate chain elongation and release. The support system is capable of withstanding mildly basic and acidic reaction conditions, while still permitting a convenient and quantitative release, either before or after removal of protecting groups from reactive groups, of synthesized oligonucleotides from a single polymeric support. Removal of the protecting groups before cleavage of the oligomer from the support permits the use of the immobilized oligomer as an affinity hybridization support for both isolating and detecting complementary polynucleic acids.

2 Claims, 4 Drawing Sheets

OTHER PUBLICATIONS

Duncan et al., "Affinity Chromatography of a Sequence-Specific DNA Binding Protein Using Teflon–Linked Oligonculeotides," *Analytical Biochemistry*, 169, 104–108 (1988).

Arnold et al., "A Novel Universal Support for DNA & RNA Synthesis," *Federation Proceedings*, 43(7), Abstr. No. 3669 (1984).

Lohrmann et al., "New Solid Supports for DNA Synthesis," *DNA*, 3(1), 122 (1984).

Kochetkov et al.(eds.), "Organic Chemistry of Nucleic Acids, Part A," Plenum Press, New York, New York, 1971, see pp. 48–51, see particularly p. 49.

March, "Advanced Organic Chemistry: Reactions, Mechanism and Structure," McGraw–Hill Book Company, New York, NY, 1968, see p. 875.

Ikehara et al. eds., "The Synthesis of Polynucleotides," *Adv. Carbohydrate Chem. and Biochem.*, 36, 135–213, only 202, 207–213 supplied (1979).

Kochetkov et al., "Structure of Nucleic Acids," Chapter 1 in *Organc Chemistry of Nucleic Acids, Part A*, Plenum Press, New York, NY, 1971, only pp. 48–49 and 91 supplied.

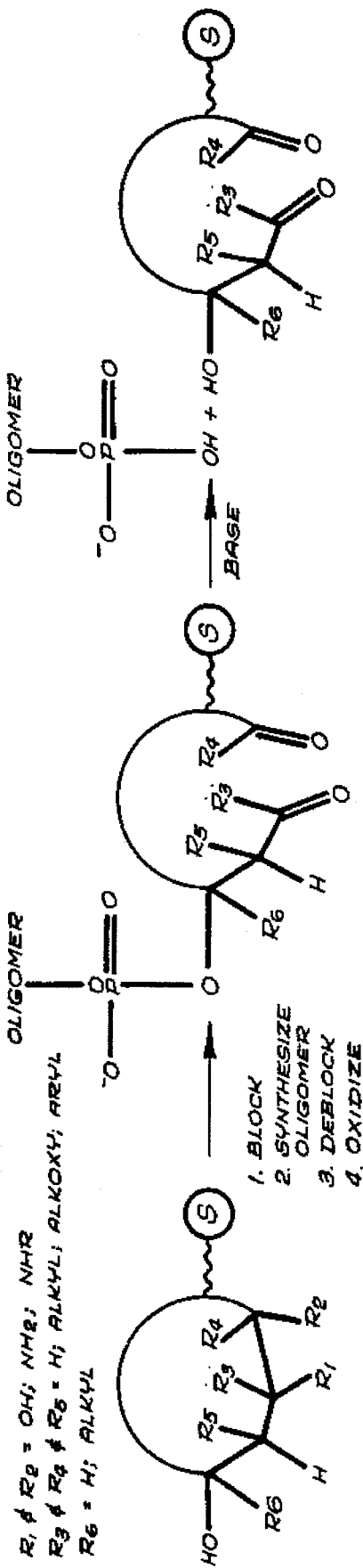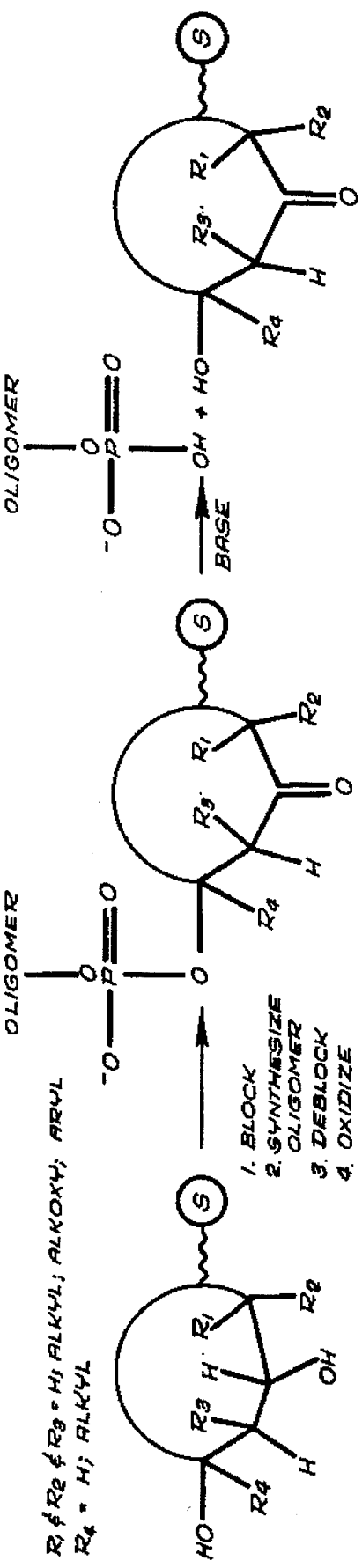

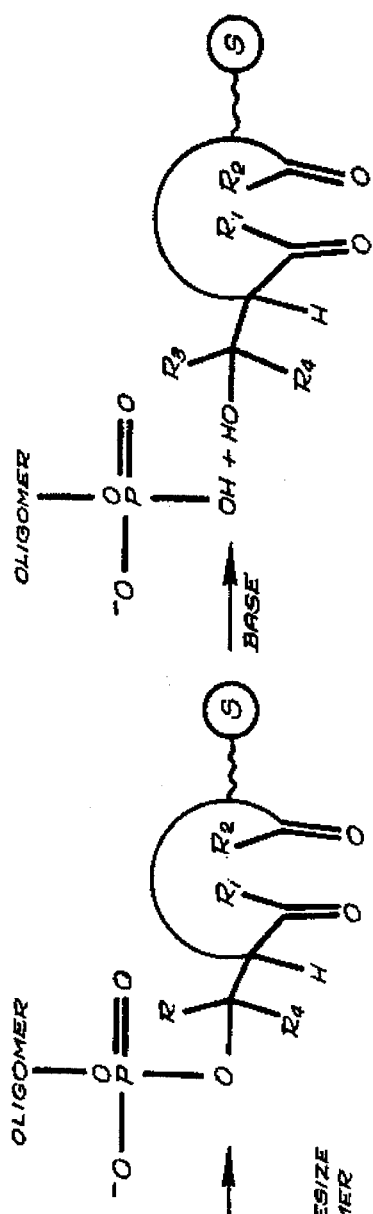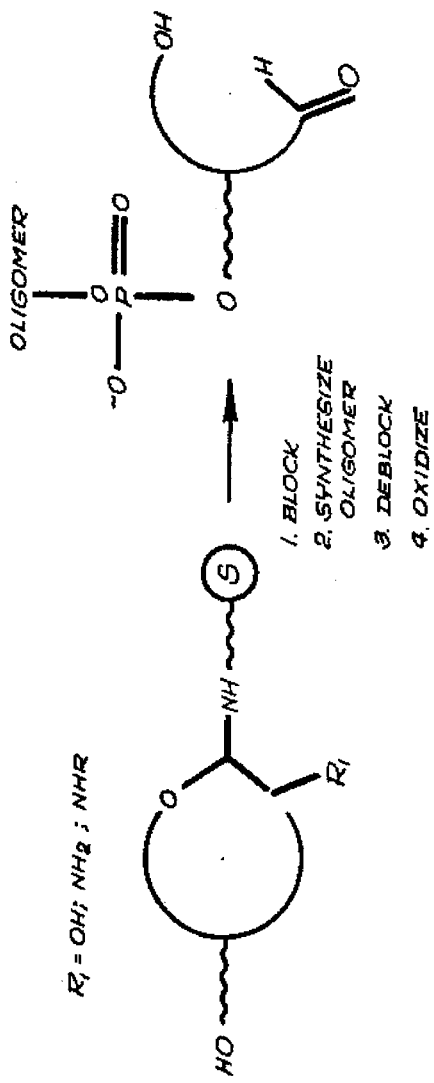
FIG. 3
FIG. 4

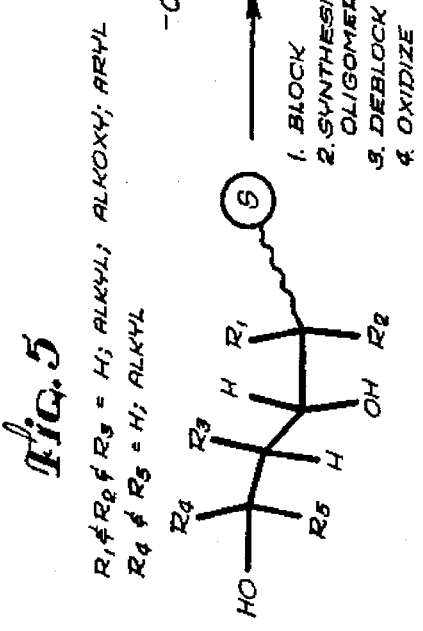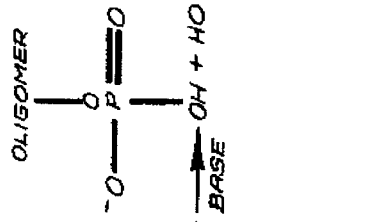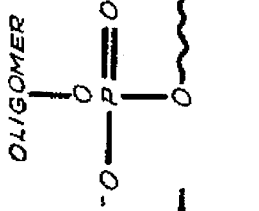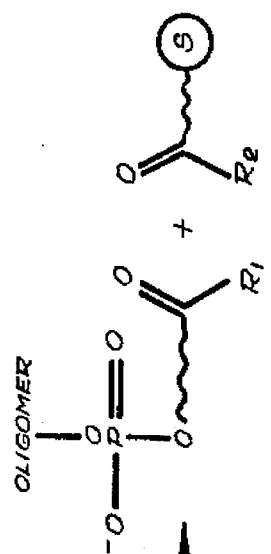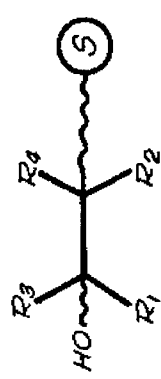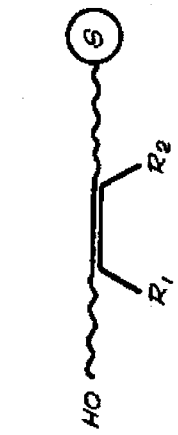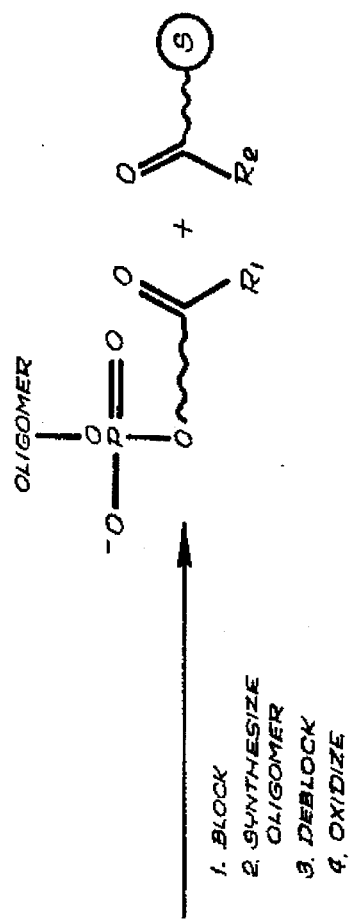

OLIGONUCLEOTIDE POLYMERIC SUPPORT SYSTEM

The application is a continuation of U.S. Ser. No. 07/492,418, filed Mar.6, 1990, now abandoned, which is a continuation of U.S. Ser. No. 07/097,298, filed Sep. 14, 1987, now abandoned, which is a continuation of U.S. Ser. No. 06/664,981, filed Oct. 6, 1984, now abandoned, which is a continuation-in-part of U.S. Ser. No. 06/528,556, filed Sep. 2, 1983, now abandoned.

BACKGROUND OF THE INVENTION

The present invention relates generally to oligonucleotide synthesis and, more particularly, to a new and improved primer system that enables oligonucleotides to be more easily and more efficiently synthesized on a solid support.

Oligonucleotides are relatively short pieces of either DNA (deoxyribonucleotides) or RNA (ribonucleotides) with chain lengths in the range of from 3–100 base units. Both deoxyribonucleotides and ribonucleotides have particular biological significance due to their key roles in cellular processes and cell growth. The component of the cell which contains the primary information for growth and protein expression is DNA. Due to the fact that it is now possible to incorporate newly synthesized pieces of DNA into the DNA of a cell, methods which facilitate the chemical synthesis of oligodeoxyribonucleotides take on particular significance. Such methods can be employed either to help correct defective genetic information or to substantially modify the proteins which an organism expresses. For example, a bacterium may be provided with the polydeoxy-ribonucleotide which contains the genetic information for the synthesis of human glucagon. Under the proper conditions, the organism would then produce human glucagon.

In addition, a range of other pharmacological, diagnostic and research applications of oligonucleotides exist. The full usefulness of oligonucleotides, however, awaits methods to effectively synthesize them in high yield and greater purity.

Until the mid-1970's, oligonucleotide synthesis was carried out in a liquid phase. The separation and purification problems associated with liquid phase techniques prevented a practical automated system for oligonucleotide synthesis. To solve these separation and purification problems, polymeric supports were developed. Up until now, use of these polymeric supports has involved the coupling of the oligonucleotide to the solid support by procedures which permit cleavage between the support and the first nucleotide. However, since the first nucleotide can be any one of four bases, these procedures have necessitated the implementation of eight different initiated supports, i.e., four for DNA and four for RNA, in order to synthesize desired oligonucleotides. It would be a significant advancement if a support system were available, with a primer (chain initiator) of great versatility, such that all desired oligonucleotides could be synthesized from a single type of polymeric support.

To be of practical utility, a polymeric support and primer must retain the growing oligonucleotide until synthesis is complete. Also, once synthesis is complete, the primer should be capable of being cleaved to permit the release of the oligonucleotide from the polymeric support. Many of the primers discussed in the literature possess linkages that are very acid or base labile. Thus, the oligonucleotide may be released from the polymeric support, at an undesirable time with resulting structural rearrangement, by treatment with acidic or basic reagents. See, e.g., M. D. Matteucci and M. H. Caruthers, *Synthesis of Deoxyoligonucleotides on a Polymer Support*, Journal of the American Chemical Society, Vol. 103, No. 11, 1981, pgs. 3185–3191, and H. Sommer and F. Cramer, *Chemische Synthese yon Desoxyoligonucleotides mit 5 - Phosphat-gruppe am Polymeren Trager (Chemical Synthesis of Deoxyoligonucleotides with 5 - Phosphate Group on a Polymer Support)*, Chem. Ber., Vol. 107, 1974, pgs. 24–33. The use of an acid labile primer, however, prevents the use of mildly acidic reagents or conditions during the oligonucleotide synthesis. Similarly, use of a base labile primer prevents the use of mildly basic reagents or conditions. Consequently, using an acid or base labile primer greatly restricts the versatility of a polymeric support system.

Primers that are very acid or very base labile also restrict the versatility of a polymeric support system in other ways. For instance, many blocking groups are ordinarily used to protect the various functions of the nucleotides, i.e., the amine or hydroxyl functions of the base, the 2' hydroxyl of ribonucleotides, the 3' and the 5' hydroxyls of deoxyribonucleotides and ribonucleotides, and the phosphate groups. Preferably, the polymeric support system is versatile enough to permit removal of these protecting groups before the oligonucleotide is released from the polymeric support or, in the alternative, the oligonucleotide can be released from the polymeric support before the protecting groups are removed. Primers that are very acid labile or very base labile, however, significantly restrict this versatility.

What is needed, therefore, is a completely versatile polymeric support system, that is, a polymeric support arrangement and corresponding method of oligonucleotide synthesis that can withstand mildly basic and mildly acidic reaction conditions and still permit a convenient and quantitative release at the desired time of all types of synthesized oligonucleotides from a single polymeric support. The present invention satisfies this need.

SUMMARY OF THE INVENTION

The present invention provides a unique polymeric support system especially useful in the synthesis of oligonucleotides. Specifically, the system of the present invention is characterized by a unique support and primer configuration and the method of oligonucleotide synthesis corresponding to that configuration. The most preferred polymeric support system of the present invention can withstand mildly acidic or basic conditions and reagents. Consequently, the most preferred primer of the present invention provides much more versatility than previously known polymeric support systems. The polymeric support system of the present invention also allows a greater flexibility in the types of conditions and reagents used to synthesize both DNA and RNA. The system of the present invention allows chain elongation in either the 3' or 5' direction, by any currently available oligonucleotide synthesis method, and also permits the oligonucleotide to be completely deprotected before release from the polymeric support or, in the alternative, permits the oligonucleotide to be released from the polymeric support before all of the protecting groups are removed. In addition, this unique polymeric support system features a universal primer which eliminates the need to synthesize eight different initiated supports depending upon whether DNA or RNA is desired to be synthesized. Cleavage of the desired oligonucleotide can be achieved with substantially quantitative results.

The polymeric support system of the present invention comprises a polymeric support and a primer covalently bonded to said polymeric support wherein the primer is cleaved by selective oxidation, that is, oxidizing one or more oxidizable substituents of the primer without oxidizing any of the other bonds of the primer or oligonucleotide. The selective oxidation either directly cleaves the primer or, in the alternative, indirectly permits the cleavage of the primer. In a direct cleavage, an effective oxidizing agent itself causes a rupture of the primer backbone which releases the oligomer from the support. In an indirect cleavage, an effective oxidizing agent activates an electron withdrawing center adjacent to the phosphate of the attached oligonucleotide which, when further treated with an effective base, causes a hydrolysis or an elimination, resulting in the release of the desired oligonucleotide.

Various oxidizable substituents may be used in accordance with the present invention. In the preferred embodiments, portions of primer having pairs of oxidizable groups vicinally related to each other or located near a phosphate electron withdrawing group comprise the oxidizable substituents of the present invention. The pair of oxidizable groups may also be an alkenyl bond in a linear or cyclic primer, with an oxidizable group being 65 to the phosphate in a more preferred embodiment. In the most preferred embodiment, the oxidizable substituent is a ribose with unblocked cis-hydroxyl groups.

The oligonucleotide synthesis method of the present invention comprises (a) selection of a polymeric support, (b) attachment of a primer to the polymeric support of step (a), wherein a portion of the primer possesses one or more oxidizable substituents, (c) protecting the oxidizable substituents of step (b) with blocking groups, (d) protecting reactive groups on the polymeric support with blocking groups, (e) condensing nucleotides onto the primer to synthesize an oligonucleotide, (f) deprotecting the oxidizable substituents after synthesis of the oligonucleotide is complete, (g) selectively oxidizing the oxidizable substituents of step (f) with an effective oxidizing agent, (h) simultaneous with or subsequent to step (g), treating the oligonucleotide with an effective base and (i) recovering the oligonucleotide.

Significantly, an oligonucleotide synthesized on the most preferred polymeric support system of the present invention is not released from the polymeric support system under mildly basic or mildly acidic conditions. Instead, the synthesized oligonucleotide is only released from the polymeric support if the oxidizable substituents are first deprotected and then selectively oxidized by an effective oxidizing agent accompanied by simultaneous or subsequent treatment with an effective base. Thus, the polymeric support system of the present invention offers great versatility. Since the synthesized oligonucleotide will only be released when an effective oxidizing agent is used, acid and base labile capping (blocking) groups used to protect the various nucleotide functions may be removed before or, alternatively, after the oligonucleotide is released from the polymeric support system. Also, mildly acidic or mildly basic conditions or reagents may be used during the oligonucleotide synthesis without releasing the oligonucleotide from the support.

There are other embodiments of the present invention wherein the polymeric support system is labile to either acidic or basic conditions yet still possesses significant utility. In those situations where it is not necessary to remove the blocking groups before cleaving the oligonucleotide from the support, stability of the support system to acid and base conditions may not be essential. For example, silica supports employed in conjunction with oxidizable primers are useful, yet are not stable to basic conditions.

Various mild oxidizing agents may be used as the effective oxidizing agents of the present invention. These oxidizing agents must be reactive with the desired cleavage sites yet be mild so as not to involve reactive groups on the oligomer. In a preferred embodiment, periodate, permanganate, dichromate, manganese dioxide or lead tetra-acetate comprises the effective oxidizing agent of the present invention. In the most preferred embodiment of the present invention, the effective oxidizing agent is periodate.

The effective base of the present invention performs one of two alternative functions. For indirect cleavages of the primer, the effective base is used simultaneously with or subsequent to the selective oxidation in order to cause a hydrolysis of the primer or an elimination of the electron withdrawing phosphate of the first nucleotide of the oligomer, thereby releasing the oligomer from the polymeric support system. Bases such as aniline, piperidine, pyridine, morpholine, triethylamine, ammonium hydroxide or sodium hydroxide may be used as the effective base of the present invention. In a preferred embodiment, bases that form Schiff bases with aldehydes such as aniline, methylamine, ethylamine and ammonia comprise the effective base of the present invention for indirect cleavages. In the most preferred embodiments, aniline or ammonium hydroxide is the effective base of the present invention for indirect cleavages.

For direct cleavages, the selective oxidation of the oxidizable substituent alone causes the cleavage of the primer. In many direct cleavages, however, portions of primer remain attached to the oligonucleotide after the oligonucleotide has been released from the polymeric support. In these situations, the effective base may be used to remove the remaining portions of primer from the released oligonucleotide. Several mild bases may be used to eliminate these remaining portions of primer from the released oligonucleotide. In a preferred embodiment, dilute sodium hydroxide, dilute ammonium hydroxide or piperidine is effectively used to clean these remaining portions of primer from the released oligonucleotide. In the most preferred embodiment, piperidine is the effective base used to remove the remaining portion of primer from the released oligonucleotide.

The polymeric support system of the present invention has particular utility as an oligonucleotide hybridization affinity system. After removal of protecting groups on the oligonucleotide, the synthesized oligonucleotide may be hybridized with complementary polynucleic acids. In the most preferred embodiment, the hybridized DNA or RNA would be conveniently and quantitatively recovered upon elution. Alternatively, the duplex may be recovered by following the oxidative cleavage procedure of the present invention. Protecting groups on the oligonucleotide and on the oxidizable substituents of the primer are first removed and the synthesized oligonucleotide is then permitted to hybridize with complementary nucleic acids. Oxidative cleavage of the primer followed by treatment with a mild base releases the duplex from the polymeric support.

In addition, such an oligonucleotide hybridization affinity system can be conveniently used for the detection of the immobilized complementary polynucleic acid. Once immobilized, the complementary polynucleic acid can be detected using various methods, as long as the recognition sites for the detection method are distinct from those involved in the immobilization of the complementary polynucleic acid to the support. Such detection methods may be colorimetric, fluorescent, luminescent, radio-label based or any other conveniently used and sufficiently sensitive procedure.

Other aspects and advantages of the present invention will become apparent from the following more detailed description of presently preferred embodiments, which disclose, by way of example, the principles of the invention.

DESCRIPTION OF THE DRAWINGS

FIGS. 1a and 2a illustrate reaction schemes for the synthesis of oligonucleotides and show the cleavage of a cyclic primer where pairs of oxidizable substituents are proximal to the phosphate of the synthesized oligomer.

FIGS. 1b and 2b illustrate reaction schemes for the synthesis of oligonucleotides and show the cleavage of a cyclic primer where a single oxidizable substituent is proximal to the phosphate of the synthesized oligomer.

FIG. 3 illustrates a reaction scheme for the synthesis of oligonucleotides and shows the cleavage of a cyclic primer where the pair of oxidizable substituents is an alkenyl bond.

FIG. 4 illustrates a reaction scheme for the synthesis of oligonucleotides and shows the cleavage of a cyclic primer where the oxidizable substituents are located at the point of attachment to the polymeric support.

FIG. 5 illustrates a reaction scheme for the synthesis of oligonucleotides and shows the cleavage of a linear primer where a single oxidizable substituent is FIG. 6 illustrates a reaction scheme for the synthesis of oligonucleotides and shows the cleavage of a linear primer where pairs of oxidizable groups are vicinally related to each other.

FIG. 7 illustrates a reaction scheme for the synthesis of oligonucleotides and shows the cleavage of a linear primer where a pair of oxidizable substituents is an alkenyl bond.

DETAILED DESCRIPTION OF THE PREFERRED EMBODIMENTS

The present invention provides a unique polymeric support system that enables convenient and versatile synthesis of oligonucleotides. The polymeric support system of the present invention comprises a polymeric support and a primer having one or more oxidizable substituents. A selective oxidation of these oxidizable substituents causes a direct cleavage of the primer or, in the alternative, permits an indirect cleavage of the primer resulting in the release of the synthesized oligonucleotide from the polymeric support.

The discovery of this polymeric support system is of particular significance. The polymeric support system of the present invention enables one to synthesize oligonucleotides which require little further purification. In addition, this polymeric support system may be used to facilitate the immobilization of either oligonucleotides or polynucleic acids which possess regions complementary to the oligonucleotide synthesized on the support. The oligonucleotide or polynucleic acid thus immobilized may be either detected using various specific detection methods or recovered for further study. The many applications of the present invention will be apparent to one skilled in the art.

A wide range of polymer supports can be used as the polymeric support of the present invention. The preferred polymer supports include polystyrenes, cross-linked polystyrenes, cross-linked polyamino acids, polyethyleneglycol, co-polymers of vinyl acetate and N-vinyl pyrrolidone, as well as other polyolefins, polyesters, polyamides, polyacrylates, polymethacrylates, metal oxides, clays, various glasses and grafts using combinations of any of these supports.

The polymeric supports of the present invention may be soluble or insoluble; preferably, however, they are insoluble. In addition, they are stable under the reactive conditions employed and contain the necessary reactive groups on their surfaces to effectuate covalent bonding of the primer to the support. While many supports are acceptable for purposes of implementing the invention disclosed herein, polymeric supports with large surface areas consisting of a great number of bonding sites in proportion to weight are most preferred.

The reactive groups on the surface of the polymer permit the primer to be covalently bonded to the polymeric support. Reactive groups that are commonly used for such purposes are hydroxyl, carboxyl and amino groups. For instance, the polymer support may be provided with a terminal carboxyl functionality which will then react with hydroxyl or amino groups of the primer. Alternatively, the polymer support can be provided with amino or hydroxyl groups which will then react with carboxyl groups of the primer. For example, groups containing carboxylate functionalities can be attached to amino groups on a solid support in the presence of an appropriate condensing agent such as dicyclohexylcarbodiimide (DCC). A primer containing a primary or an aryl amine can be covalently attached to the support through condensation of the amine with the carboxylate function to form an amide. In an analogous fashion, an acid halide may be reacted with amine containing primers to form amides. Alternatively, the primer may possess an acid halide and the support may contain the amine function.

There are many other methods of attaching the primer to the support. These alternatives include Grignard condensations, ether linkage formations, Freidel-Craft alkylations, secondary amine formations, mercury salt and olefin condensations. One of ordinary skill in the art, however, can readily determine an appropriate polymeric support for a particular synthesis as well as the appropriate means for linking the primer to the polymeric support (P. Hodge and D. C. Sherrington, *Polymer Supported Reactions in Organic Synthesis*, John Wiley & Sons, New York, 1980).

Prior to using primerized support systems for oligonucleotide synthesis, reactive groups on both the support and the primer must be protected in order to prevent side reactions which will decrease the yield of the oligonucleotide. In the case of the primer this is most easily accomplished by converting reactive amines to amides, and esterifying the alcohols with the exception of the one which will participate in chain initiation. Both of these reactions take place with acid anhydrides (such as acetic anhydride in pyridine), as well as acid chlorides and other acylating agents. Protection of reactive groups on the support is dependent upon the support employed. Reactive groups on may be protected will be apparent to one of ordinary skill in the art. (Reese, C. B., Tetrahedron 34:3143–3179 (1978) and T. W. Greene, *Protective Groups in Organic Synthesis*, John Wiley & Sons, New York, 1981.)

The primer of the present invention may be embodied in many separate forms. All of these separate embodiments, however, have one feature in common: in each embodiment, the primer possesses one or more oxidizable substituents. Selectively oxidizing these substituents, without disrupting any other bonds of the primer or oligonucleotide, either directly or indirectly releases the desired oligonucleotide from the polymeric support. By utilizing a primer possessing one or more oxidizable substituents, the present invention eliminates the necessity, in the present state of the art, of fabricating eight different initiated supports.

Figure 1A:
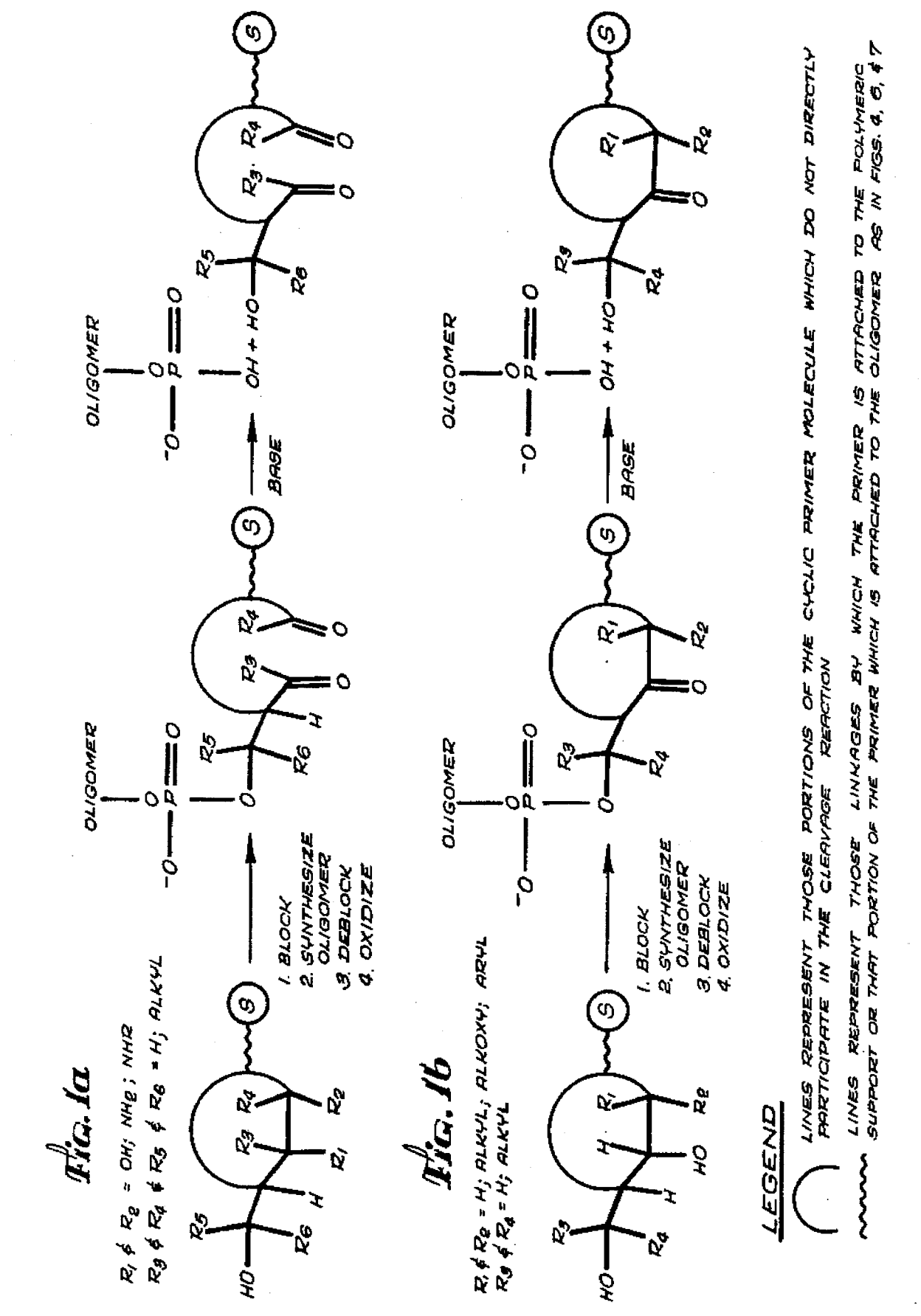

The preferred oxidizable substituents of the present invention are hydroxyl, alkenyl, primary amine and secondary amine groups. FIGS. 1, 2, 4, 5 and 6, corresponding to the preferred embodiments, demonstrate which oxidizable groups are preferred at particular bonding sites. However, these drawings are merely intended to be illustrative of the various primer structures in accordance with the present invention. One having ordinary skill in the art will apppreciate that the structures portrayed, and particularly the cyclic structures, are inherently flexible such that they may have several different embodiments without departing from the spirit and scope of the present invention.

In the presently most preferred embodiment, the oxidizable substituent is a ribonucleoside. The ribonucleoside is linked to the polymeric support through its base. The first nucleotide of the oligonucleotide to be synthesized is condensed onto the ribonucleoside and is linked to the ribonucleoside by means of a phosphate bridge between the 5' position of the ribonucleoside and the 3' position of the first nucleotide.

There are other preferred embodiments of the present invention where it is not necessary to protect and deprotect the oxidizable substituents of the primer in order to facilitate the oxidative cleavage of the synthesized oligonucleotide from the polymeric support. FIGS. 3 and 7 are illustrative of those embodiments of the present invention wherein the oxidizable substituent is an alkenyl bond. The oxidizing agent of the present invention cleaves the primer molecule at the site of the alkenyl bond. Thus, it is not necessary to proceed with steps (c) and (f) of the oligonucleotide synthesis method of the present invention since there are no oxidizable substituents in these embodiments which will undergo side reactions during the oligonucleotide synthesis step. Once again, one having ordinary skill in the art will appreciate that FIGS. 3 and 7 are inherently flexible and are intended to be illustrative of preferred embodiments of the present invention.

The primer of this unique support system allows chain elongation in either the 3' or 5' direction and is suitable for synthesizing all desired oligonucleotides. Synthesis may be conducted by many means, including the phosphite and phosphotriester methods. By way of example, oligonucleotides may be synthesized in accordance with those methods described in M. D. Matteucci and M. H. Caruthers, *Synthesis of Deoxyoligonucleotides on a Polymer Support*, Journal of the American Chemical Society, Vol. 103, No. 11, 1981 and M. J. Gait et al., *Rapid Synthesis of Oligodeoxyribonucleotides IV. Improved Solid Phase Synthesis of Oligodeoxyribonucleotides through Phosphotriester Intermediates*, Nucleic Acids Research, Vol. 8, No. 5, 1980.

The primers of the present invention may be linear or cyclic in their structure. In addition, these primers may be cleaved in one of two ways: either directly or indirectly. In a direct cleavage, the oxidation serves to cleave the primer such that the synthesized oligonucleotide is released from the support in one chemical reaction. In some situations, however, a portion of the primer remains attached to the oligonucleotide. At this point the oligonucleotide may be treated with an effective base to remove the remaining primer portion from the oligonucleotide. In an indirect cleavage, oxidation in conjunction with treatment by an effective base serves to eliminate the synthesized oligonucleotide from the support.

In a preferred embodiment of the present invention, a cyclic primer contains one or more oxidizable groups which are proximal to the phosphate of the formed oligonucleotide. After oxidation, treatment with an appropriate base eliminates the oligomer from the support. FIGS. 1, 2 and 3 are illustrative of this embodiment of the invention.

In another preferred embodiment of the present invention, a cyclic primer contains oxidizable groups located at its point of attachment with the support. In this case oxidation cleaves the oligomer and a portion of the primer from the support. Upon treatment with an appropriate base, the residual portion of the primer may be removed from the oligomer. FIG. 4 is illustrative of this embodiment of the invention.

In a third embodiment, a linear primer contains a single oxidizable group proximal to the phosphate of the synthesized oligomer. Simultaneous with or subsequent to oxidation, treatment with an appropriate base cleaves the oligomer from the support. FIG. 5 is illustrative of this embodiment of the invention.

In a fourth embodiment of the present invention, a linear primer may contain two or more adjacent oxidizable groups. Upon oxidation, this arrangement permits direct cleavage of the oligomer from the support. FIGS. 6 and 7 are illustrative of this embodiment. Again, an appropriate base may be used to cleave the residual portion of the primer from the oligomer.

While there are several positional relationships between the oxidizable function and the initiation site for oligonucleotide synthesis with respect to any particular primer, an orientation with the oxidizable function in the γ position to the phosphate is preferred for the subsequent removal of primer moiety from the synthesized oligonucleotide following cleavage from the polymeric support. One having ordinary skill in the art will appreciate that the oligonucleotide synthesis method of the present invention is still effective where the oxidizable function is in a position other than γ to the phosphate. However, the preferred embodiments of the present invention permit a more convenient synthesis of the desired oligonucleotide.

Removal of the protecting groups on the oxidizable substituents may be necessary before the cleavage of the synthesized oligonucleotide from the polymeric support. FIGS. 1, 2, 4, 5 and 6 are illustrative of this embodiment of the present invention. Deprotection is accomplished by procedures that are known to one having ordinary skill in the art. T. W. Greene, *Protective Groups in Organic Synthesis*, John Wiley & Sons, New York, 1981.

The synthesized oligonucleotide is directly or indirectly released from the polymeric support by a selective oxidation of the oxidizable substituents of the primer. This cleavage results in a yield of oligonucleotide that is substantially quantitative. For a direct cleavage, a selective oxidation comprises treating the oligonucleotide with an effective oxidizing agent. If any portions of primer remain attached to the oligonucleotide after its release from the polymeric support, these remaining portions may be removed by treatment with an effective base. In a direct cleavage, it is preferred that the carbonyl group that results from oxidation be γ to the phosphate of the synthesized oligomer. This embodiment ensures that the application of the base will be effective in cleaving the remaining portions of the primer from the synthesized oligonucleotide. Otherwise, there are embodiments of the present invention wherein treatment with the effective base will not result in complete removal of the residual primer from the oligomer. However, one having ordinary skill in the art will appreciate that these remaining portions of primer may be removed in many instances, through alternate procedures, depending upon the particular chemistry of the residual primer moiety (T. W. Greene, *Protective Groups in Organic Synthesis*, John Wiley & Sons, New York, 1981). For an indirect cleavage, a selective oxidation comprises treating the oligonucleotide with an effective oxidizing agent accompanied by a simultaneous or subsequent treatment with an effective base.

An effective oxidizing agent for both the direct and indirect cleavages comprises a mild oxidizing agent which will select for the desired cleavage sites and not for other reactive groups on the oligomer. In a presently preferred embodiment, the effective oxidizing agent is selected from the group consisting of periodate, permanganate, dichromate, manganese dioxide, and lead tetraacetate. Most preferably, periodate is the effective oxidizing agent.

For indirect cleavages, the effective base cooperates with the effective oxidizing agent to cleave the primer. An effective base for indirect cleavages comprises bases such as piperidine, pyridine, morpholine, ammonium hydroxide, sodium hydroxide and bases that form Schiff bases with aldehydes. Preferably, an effective base for indirect cleavages is a base that forms Schiff bases with aldehydes, such as aniline, methylamine, ethylamine, n-propylamine, and ammonia. Most preferably, the effective base for indirect cleavages is aniline, ammonium hydroxide, or n-propylamine.

For direct cleavages, the effective base used to remove any portions of primer remaining attached to the released oligonucleotide comprises mild bases. In a preferred embodiment, the effective base for direct cleavage is dilute sodium hydroxide, ammonium hydroxide, piperidine, or n-propylamine. Most preferably, the effective base used in conjunction with a direct cleavage is piperidine.

In the most preferred embodiment of the present invention, the oxidizable substituent of the primer is a ribonucleoside and the first nucleotide of the oligoncleotide to be synthesized is linked to the ribonucleoside via the 5' position of the ribonucleoside. FIG. 1a is a reaction scheme which illustrates this embodiment of the present invention. Where $R_1$ & $R_2$=OH and $R_3$ & $R_4$=H, $R_1$ & $R_2$ would correspond to the 2' and 3' hydroxyls of a ribose ring in FIG. 1a. During oligonucleotide synthesis, the 2' and the 3' position of the ribonucleoside are blocked. The oligonucleotide is cleaved from the polymeric support by first deblocking the 2' and 3' hydroxyl groups. The oligonucleotide is then released from the polymeric support by a selective oxidation which indirectly cleaves the primer. The effective oxidizing agent is periodate and the effective base is aniline, ammonium hydroxide, or n-propylamine. Alternatively, the oligonucleotide may be first treated with periodate, followed by treatment with aniline, ammonium hydroxide, or n-propylamine, or the oligonucleotide may be treated simultaneously with periodate and aniline. The synthesized oligonucleotide is then recovered using standard techniques.

Removal of the protecting groups on the oligomer may be undertaken either before or after the oxidative cleavage of the synthesized oligonucleotide from the support. In the situation where it is desired to remove the protecting groups before cleavage, sodium hydroxide or ammonium hydroxide may be used to remove the protecting groups on the bases. Where methyl or trichloroethyl are the protecting groups on phosphorus, the preferred reagents for deprotection are ammonium hydroxide or thiophenoxide. Tributylphosphine is the preferred reagent for the removal of 2,2,2-trichloro-1,1-dimethylethyl as the protecting group on phosphorus. Where o-chlorophenol and p-chlorophenol are the protecting groups on phosphorus, oximates such as benzyloximate and pyridinaldoximate may be employed as the preferred deprotecting agents in accordance with those methods delineated in M. J. Gait et al, *Rapid Synthesis of Oligodeoxyribonucleotides IV. Improved Solid Phase Synthesis of Oligodeoxyribonucleotides through Phospho-triester Intermediates,* Nucleic Acids Research, Vol. 8, No. 5, 1980.

There are situations where it may be desirable to cleave the synthesized oligomer from the polymeric support before the removal of the protecting groups on the oligomer. The protecting groups may be removed in accordance with those procedures described in T. W. Greene, *Protective Groups in Organic Synthesis,* John Wiley & Sons, New York, 1981. This aspect of the present invention has utility where the primer does not require prior deprotection for oxidative cleavage or in those cases where protecting groups can be removed under very mild conditions. The polymeric support system and oligonucleotide synthesis method of the present invention have particular utility in facilitating oligonucleotide hybridization techniques. The support of the present invention may be used as an oligonucleotide hybridization affinity system wherein, after deprotection of the synthesized oligonucleotide (step f), it may be hybridized with complementary polynucleic acids.

In some instances, it may be desired to recover the complementary polynucleic acid that becomes hybridized to the synthesized oligonucleotide. In the most preferred embodiment of the present invention, the complementary hybridized DNA or RNA may be conveniently and quantitatively recovered upon elution. Another preferred embodiment permits the quantitative recovery of the entire duplex by the oxidative cleavage of the primer from the polymeric support in accordance with the method of the present invent ion. In this embodiment, the protecting groups on the synthesized oligonucleotide and on the oxidizable substituents of the primer are removed before hybridization. Once hybridization has been accomplished, treatment of the oxidizable substituents of the primer with an effective oxidizing agent, followed by treatment with a mild base, effectuates the release of the duplex from the polymeric support. One having skill in the art will appreciate the convenience with which hybridization products may be recovered by employing the techniques described herein.

In other cases, it may be desired merely to detect the presence of the hybridized complementary polynucleic acid, without actually removing it from the support. In this situation, several detection methods are possible, all of which are well known in the art. One such detection method employs a hybridization probe that i s complementary to a portion of the already hybridized polynucleic acid. This hybridization probe is by definition an oligonucleotide or polynucleic acid. If the complementary polynucleic acid did in fact hybridize to the synthesized oligonucleotide, then the hybridization probe will hybridize to the polynucleic acid on the support. The hybridization probe is labeled in some manner so that its presence on the already hybridized polynucleic acid after the second hybridization can be detected. Labeling techniques commonly include radiolabeling, fluorescent labeling, reporter group labeling for interaction with a protein mediated detection system, color generation and light generation. A protein mediated detection system might also be used directly. One skilled in the art will also appreciate other methods by which the hybridization probe may be labeled for later observation after the second hybridization, or alternate methods by which the hybridized complementary polynucleic acid can be detected, such as detection with specific antibodies.

The present invention is illustrated by, but not limited to, the following examples.

EXAMPLE 1

SYNTHESIS OF ADENOSINE-N⁶-DODECYLAMINE ATTACHED TO A METHACRYLATE POLYMER

5-DIMETHOXYTRITYL-6-CHLOROPURINERIBOSIDE (I)

A solution of 6-Chloropurineriboside (287 mg.) and dimethoxytritylchloride (350 mg.) in anhydrous pyridine (1 ml) was kept at room temperature. After 1.5 hours an aliquot checked by TLC analysis on silica showed that the reaction was better than 95% complete. The mixture was then poured on ice-NaCl and extracted with $CH_2Cl_2$. The organic layer was washed repeatedly with aqueous NaCl, then dried over $Na_2SO_4$ and evaporated in vacuo. The residual foam was finally dissolved in benzene and lyophilized.

5'-DIMETHOXYTRITYL-N⁶-[12-AMINODODECYLAMINE]-ADENOSINE (II)

A mixture of (I) and 1,12-diaminododecane (2 g.) in anhydrous toluene (14 ml) was kept at 100° C. for 20 min. before it was added dropwise to hexane (150 ml) with vigorous stirring. The precipitate which formed in hexane was collected by centrifugation, then dissolved in $CH_2Cl_2$, and the organic solution briefly extracted with aqueous KOH (0.05M). The organic layer was dried over $Na_2SO_4$ and evaporated until dry. Subsequently, the solid residue was dissolved in warm toulene. After removing a small amount of insoluble material, the dissolved material was precipitated by dropwise addition of excess hexane. The white precipitate which formed was collected by centrifugation, washed with hexane and dried in vacuo. The yield was 524 mg. as a fine powder.

COUPLING TO THE SUPPORT

Amberlite CG50 (100–200 wet mesh) was thoroughly washed with aqueous 0.1M HCl, then with 0.15M HCl in 30% aqueous methanol, followed by washings with methanol, acetone, chloroform and ether. The resulting powder was dried in vacuo over $P_2O_5$.

A mixture of pretreated amberlite (1 g.) and carbonyldiimidazole (660 mg.) in dimethylformamide (DMF) (5 ml) was shaken for 4 hours at room temperature. The activated amberlite was washed free of excess carbonyl-diimidazole with DMF before it was suspended in a solution of (II) in DMF (6 ml) and triethylamine (0.5 ml). The mixture was then heated to 80° C. for 1 hour with stirring. The unreacted carboxyl groups were capped by activating them with carbonyldiimidazole and dimethylamine in DMF (3.5 ml) followed by shaking for 1 hour at room temperature. The resin was filtered off, then washed with acetone and ether. The dry powder was suspended in a mixture of acetic anhydride (4 ml) and anhydrous pyridine (10 ml). After 24 hours the resin was filtered off, carefully washed with acetone followed by ether, and dried.

Dimethoxytrityl release indicated that the primer density was between 50–100 microequivalents per gram.

EXAMPLE 2

SYNTHESIS OF URIDINE ATTACHED TO A STYRENE-DIVINYLBENZENE COPOLYMER

PREPARATION OF URIDINE-STYRENE-DIVINYLBENZENE COPOLYMER RESINS

The nucleoside 5-(3-amino-propenyl)-uridine was synthesized according to the procedure described in Ruth et al, J. Org. Chem., 43:2870 (1978) and dissolved in 1:1 methanol/dioxane (200 mls). 3.6 grams of chloromethylstyrene beads (BIOBEADS XS-1, 1.25 mmoles of chlorine/gram of bead) were added followed by swirling in a rotary shaker at 200 rpm for 30 hours at 65° C. The support was then filtered and washed successively with tetrahydrofuran, water, methanol and tetrahydrofuran before drying under high vacuum for one hour. Tetrahydrofuran (40 mls) and triethylamine (15 mls) were added next followed by swirling at 200 rpm for one hour at 50° C. The support was then filtered, washed successively with water, methanol, chloroform and ether, and dried under high vacuum for 8–18 hours at room temperature.

Ten percent acetic anhydride in pyridine (1:9, 20 ml/gram of resin) and dimethylaminopyridine (2 mg/gram of resin) were added to the dried resin followed by swirling for one hour at 40° C. After cooling, the liquid phase was decanted and the resin was washed successively with pyridine, chloroform and methanol before being lyopholized for 8–18 hours. Pyridine in concentrated ammonium hydroxide (1:1, 200 ml/gram of resin) was then added with swirling for 4 hours at 37° C. Upon evaporation to dryness under reduced pressure, a small amount of pyridine was added and the resin was once again evaporated to dryness. Fifteen mls of pyridine/gram of resin was then added, together with 80 mgs of dimethoxytrityl chloride/gram of resin, and the mixture was swirled for 3 hours at 70° C. The resin was then filtered, washed successively with chloroform, methanol and ether, and briefly vacuum dried. Twenty percent acetic anhydride in pyridine (10 mls/gram of resin) was then added and swirled for 8–18 hours at 37° C. Finally, the resin was filtered, washed successively with pyridine, chloroform and ether, and dried under vacuum for 8–18 hours at room temperature.

Dimethoxytrityl releases indicated that the primer density was between 10–50 microequivalents/gram.

EXAMPLE 3

SYNTHESIS OF ADENOSINE-N⁶-DODECYLAMINE ON POLYACRYLMORPHOLIDE

A mixture of polyacrylmorpholide resin (Vega Biochemicals-Catalogue No. 18964) (1.95 g) and 1,12-diaminododecane (2 g.) in 12.5 ml of freshly distilled glycol was heated under $N_2$ at 180° C., with simultaneous stirring, for 20 hours. The resin was collected by centrifugation and then thoroughly washed sequentially with methanol, 10% acetic acid-methanol (1:1), methanol-triethylamine, methanol, and finally ether. The resin was dried in vacuo yielding 1.61 g. of a fine yellowish power. An aliquot tested with picrylsulfonate in borate buffer (pH 9.7) turned a strong orange color, indicating a good substitution of morpholine by the diamine.

A mixture of the above resin (860 mg.), 5'-dimethoxytrityl-6-chloropurineriboside (470 mg.), anhydrous toluene (5 ml) and triethylamine (300 microliters) was heated at 60°–70° C., with stirring, for 20 hours. The resin was collected by centrifugation, then washed sequentially with toluene, methanol-triethylamine, methanol and ether. After drying the resin in vacuo, it was suspended in pyridine (6 ml) and acetic anhydride (1.5 ml) and shaken for 8–18 hours. The resin was then washed with pyridine, pyridine-water, methanol, acetone and ether.

Quantitation of the dimethoxytrityl removal with 2.6% trichloroacetic acid in chloroform indicated that the primer density was 20 microequivalents/gram.

EXAMPLE 4

OXIDATIVE REMOVAL OF OLIGOMERS FROM THE SUPPORT

Once the oligomers have been synthesized on the primer-support system through the utilization of standard techniques, they may be easily removed using a combination of either periodate and ammonium hydroxide or periodate and aniline. When methyl is used as the phosphate protecting group, the support bound oligomer-primer is first incubated for 8-18 hours at 50° C. in concentrated ammonium hydroxide. This procedure removes all the blocking groups including those on the cis-diol. After washing the support bound oligomer-primer with appropriate solvents, including water, acetone and dichloromethane, the oligomer is oxidized by incubation (30 minutes-several hours) in 0.05M sodium periodate/0.05M sodium acetate (pH 5.0–7.3). After washing with water, concentrated ammonium hydroxide is added and the mixture is then incubated for several hours at room temperature. The oligomer obtained is nearly free of contaminating species upon filtration, followed by washing with water and 50% ethanol. After lyophilization to remove the water, ammonium hydroxide and ethanol, the desired oligomer is purified further by standard procedures.

Alternatively, after the incubation in sodium periodate/acetate, the oligomer may be removed by incubation with aniline (pH 5.0) for several hours. The oxidative removal of the synthesized oligonucleotide from the support may be carried out either before or after deprotection of the reactive groups on the oligomer and support.

As a test of the cleavage procedure, a monomeric unit of 5'-dimethoxytrityl-N-benzoyl-2'-deoxycytidine was coupled to the polymethacrylate support (Example 1) of the present invention. Using standard phosphomonochlorodite chemistry (Mateucci, M. D. and Caruthers, M. H., Tetrahedron Letters, 21:719–722 [1980]), 12 mls of a 20 mM solution of the activated nucleoside in acetonitrile/4% 2,6-lutidine was added to 533 mgs of the support. After completion of the oxidation step, the support was washed successively with acetone, dichloromethane, water, acetone, dichloromethane and ether followed by air drying.

The following procedures were followed in order to recover the monomer from the support. Initially, the monomer was treated with concentrated ammonium hydroxide for 8–18 hours at 50° C. After washing with ammonium hydroxide, acetone and dichloromethane followed by drying under a stream of nitrogen, a mixture of 0.05M sodium acetate and 0.05M sodium periodate (10 mls, pH 7.2) was added and the entire mixture was incubated for a period of 24 hours at room temperature. Upon washing with water, acetone, and dichloromethane followed by drying under nitrogen, concentrated ammonium hydroxide (10 mls) was added and the mixture was once again incubated for 24 hours at room temperature. After a final washing with ammonium hydroxide, the monomer was recovered in good yield from the support.

For this particular procedure, a slightly elevated pH was employed during the periodate oxidation in order to prevent the loss of the dimethoxytrityl group which was used for quantitation.

EXAMPLE 5

SYNTHESIS OF 5'-DIMETHOXYTRITYL-2',3' DIACETYLADENOSINE-$N^6$-CAPROIC ACID ATTACHED TO A TEFLON/COPOLYMER GRAFT

The following example represents the most preferred embodiment of the present invention.

5'-Dimethoxytrityl-6-chloropurineriboside was prepared as described in Example 1. 5'-Dimethoxytrityl- 6-chloropurineriboside (3.0 g, 5 m mole) was then reacted with 6.75 g, (52 m mole) 6-aminocaproic acid in acetonitrile (30 ml), N-ethyldiisopropylamine (8 ml) and $H_2O$ (25 ml) at 80° C. for 15 hours to produce the 5'-dimethoxytrityladenosine-$N^6$-caproic acid salt. The product was purified by chromatography on a silica column and eluted with a linear gradient of methanol (~20%) in chloroform containing 2% triethylamine.

After evaporation of the solvent followed by evaporation from a small amount of pyridine, the syrupy 5'-dimethoxytrityl adenosine-$N^6$-caproic acid salt was acetylated in anhydrous pyridine (50 ml) using acetic anhydride (10 ml) for 24 hours at room temperature in the dark. The product, 5'-dimethoxytrityl-2', 3'-diacetyl adenosine-$N^6$-caproic acid triethylamine salt, was isolated by pouring the reaction mixture on ice, extracting the organic phase with dichloromethane and drying the dichloromethane phase with anhydrous sodium sulfate, followed by rota-evaporation of the solvent. The residual syrup was dissolved in 80 mls of toluene and the desired compound precipitated by the addition of 420 mls hexane. After filtration and air drying, the product yield was 2.62 g (2.4 m moles).

The 5'-dimethoxytrityl-2', 3'-diacetyl adenosine-$N^6$-caproic acid triethylamine salt (0.62 g, 0.56 m moles) was reacted with 1.04 g (5 m moles) dicyclohexylcarbodiimide and 0.54 g (4 m moles) 1-hydroxybenzotriazole in acetonitrile (20 ml) and anhydrous pyridine (4 ml) at 20° C. for four hours in order to form the active ester at the caproic acid site. A Teflon wool/copolymer grafted support (9.18 g) which contained alkylamine groups eight atoms in length was added and the mixture incubated for 19 hours at 20° C.

The support was washed with acetonitrile methanol containing 2% triethylamine, methanol and ether in order to remove any uncoupled nucleosides. Unreacted amine groups on the support were then capped with excess acetic anhydride (5 ml) and N-ethyldiisopropylamine (2 ml) in 50 mls pyridine for two hours at 20° C. with shaking. After washing with acetonitrile, methanol and ether, the dimethoxytrityl content of the support indicated that the primer density was approximately 30 microequivalents per gram.

EXAMPLE 6

THE SYNTHESIS OF $(dTp)_{15}$ USING THE 5'-DIMETHOXYTRITYL 2',3'-DIACETYLADENOSINE-$N^6$-CAPROIC ACID TEFLON/COPOLYMER GRAFT SUPPORT (TEF I)

An oligomer 15 thymidines in length was synthesized on 0.105 g of the TEF I support with a Biosearch Sam One DNA Synthesizer using the modified triester chemistry of Efimov (V. A. Efimov, Nuc. Acid Res. , 10, 6675 (1982)). Once synthesis was complete, the phosphate protecting groups were removed with tetramethylguanidine and pyridinealdoxime in acetonoitrile according to standard procedures (Reese, C. B. and Yan Kui, Y. T. , Chem. Comm. 802 (1977)). The base protecting groups were then removed by incubation with concentrated $NH_4OH$ at 55° C. for five hours. These deprotection procedures also removed the 2' and 3' protecting groups on the adenosine.

The support bound oligomer was then treated with 0.05M $NaIO_4$ in 0.02M $Na_2HPO_4$, (pH=7.2) containing 20% acetonitrile for three hours in the dark. After washing in $H_2O$, the oligomer was cleaved from the support with a mixture of 5% n-propylamine and 10% acetonitrile in 1M Triethylammonium bicarbonate (2–3 hours). Upon filtration and washing the support with a mixture of water and ethanol, the oligomer containing supernatant was evaporated to dryness in the presence of a small amount of tributylamine.

HPLC analysis with a Unimetrics RP-8 column eluted with a linear gradient of 3–30% acetonitrile (over 60 min.) in 0.025M ammonium acetate, pH=7.1 gave a major peak at approximately 54 min. which is consistent with a 5'-dimethoxytrityl $(dTp)_{15}$.

The authenticity of the material was confirmed by removing the dimethoxytrityl group with 80% acetic acid, kinasing the oligomer with $^{32}P$ ATP by standard procedures (Johnson, R. A. and Walset, T. F., Adv. in Cyclic Nucleotide Res., Volume 10, edited by G. Brooker, P. Greengard and G. A. Robison, Raven Press, New York, 1979) and electrophoresing the radiolabeled oligomer on a 20% polyacrylamide gel by standard procedures (Maniatis, T. , Fritsch, E. F. and Sambrook, J. , Molecular Cloning, Cold Spring Harbor Laboratory, 1982). After autoradiography, the oligomer was shown to be virtually a single spot with the mobility of $(dTp)_{15}$.

EXAMPLE 7

SYNTHESIS OF ADENOSINE-N-6-DODECYLAMINE ATTACHED TO A TEFLON/COPOLYMER GRAFT SUPPORT (TEF II)

A Teflon wool/copolymer graft containing carboxyl groups on its surface was used. The linker-arm carboxyl moieties on the support, which were 15 atoms in length, were activated by incubating 2.5 g of support with 675 mg (5 m mole) 1-hydroxybenzotriazole and 1.13 g (5.4 m mole) dicyclohexyl-carbodiimide in a mixture of acetonitrile (50 mls) and pyridine (10 ml). After incubating three hours, 1.2 g of 5'-dimethoxytrityl-adenosine-N 6-dodecylamine prepared as in Example 1 was added and the mixture shaken for 18 hours at room temperature. Dimethylamine (1.5 g, 33 m moles) in 10 mls dimethylformamide was then added and incubated for one hour at room temperature in order to convert unreacted active esters to dimethylamides.

After washing the support with acetonitrile, methanol and ether, the 2' and 3' hydroxyl groups on the adenosine were capped with a mixture of 6 mls (64 m mole) acetic anhydride and 750 mgs (6 m mole) dimethylaminopyridine in 40 mls anhydrous pyridine followed by incubating for three hours at room temperature. Acetyl chloride (2 mls, 28 m moles) was then added and the incubation continued for one hour.

The support was washed with acetonitrile, methanol and ether. The yield was 2.6 g and dimethoxytrityl release indicated that the TEF II support had a primer density of 85 microequivalents per gram.

EXAMPLE 8

THE ADDITION OF 5'-DIMETHOXYTRITYL-3'-(p-CHLOROPHENYLPHOSPHATE)-5-(METHYL-$^{14}$C) THYMIDINE TO A TEF II SUPPORT AND ITS CLEAVAGE FROM THE SUPPORT

An appropriate radiolabeled thymidine nucleotide was obtained, condensed onto the TEF II support of Example 7 and selectively cleaved from the support. This procedure verified the selective cleavage aspects of the support.

5'-Dimethoxytrityl-3'-(p-chlorophenyl phosphate)-5-(methyl-$^{14}$C) thymidine was prepared as follows. Cold thymidine (122 mg, 0.5 m moles) was combined with 5-(methyl-$^{14}$C) thymidine (Approximately 95 µCi/µmole, dissolved in water, lyophilized and dried over phosphorous pentoxide. The $^{14}$C-thymidine mixture was then dissolved in 4 ml anhydrous pyridine and evaporated to 2 ml. Dimethoxytrityl chloride (170 mg, 0.5 m mole) was then added and allowed to incubate for one hour at room temperature. The reaction mixture was then poured into ice and extracted into dichloromethane. The dichloromethane phase was dried over sodium sulfate, filtered and roto-evaporated to a gum. The gum was recrystallized at 0° C. from boiling benzene containing 2.5% triethylamine. The crystals were washed with cold benzene/cyclohexane (2:1) and dried in vacuo. The yield was 270 mg (approximately 0.5 m mole) and the radio-labeling gave 16100 cpm/O.D. at 267 nm. The $^{14}$C labeled 5'-Dimethoxytrityl thymidine was stored as a stock solution in 1 ml of anhydrous pyridine.

The $^{14}$C labeled thymidine analogue was then phosphorylated by combining 245 mg (1 m mole) p-chlorophenyl dichlorophosphate in 1.2 ml anhydrous pyridine, 18.5 µl $H_2O$ and adding 400 µl of the 5'- Dimethoxytrityl- 5-(methyl-$^{14}$C) thymidine stock, which was dissolved in pyridine. After 30 min. at room temperature, approximately 10 ml of 1M triethylammonium bicarbonate was added and the organic phase extracted 3 times with ethyl acetate. The organic phase was back extracted with an aqueous NaCl solution and dried over sodium sulfate. The organic phase was then filtered, evaporated to dryness, and lyophilized from dioxane which contained a trace of triethylamine. The lyophilized material was dissolved in 3 ml anhydrous pyridine and stored at 4° C. Thin layer chromatography on silica gel plates using 10% methanol in chloroform containing 2% triethylamine as the eluting solvent indicated that the product was chromatagraphically pure. Scintillation counting indicated that there was 11.5 µCi of material present.

Forty-one micromoles of the $^{14}$C labeled thymidine analogue were condensed with 50 mgs of the TEF II support using the modified triester method of Efimov (V. A. Efimov, Nuc. Acid Res., 10, 6675 (1982)). The deprotecting and cleavage steps disclosed in Example 5 were then carried out and the nucleotide release monitored by the release of $^{14}$C at each step. The results are summarized as follows:

| Step | % $^{14}$C on Support | % $^{14}$C in Solution |
| --- | --- | --- |
| Before NH$_4$OH deblocking | 100 | 0 |
| After NH$_4$OH (50° C., 20 hrs.) | 97 | 3 |
| After periodate oxidation | 96 | 1 |
| After selective base cleavage | 18 | 78 |

This example verifies that upon oxidation followed by base treatment, the selective cleavage site splits as desired.

EXAMPLE 9

UTILIZATION OF A POLYMETHACRYLATE SUPPORT SYSTEM TO SYNTHESIZE A DNA HYBRIDIZATION AFFINITY COLUMN

To illustrate a practical application of the present invention, a polymethacrylate support system has been effectively utilized as a sequence specific affinity support for nucleic acid separations.

A polymethacrylate support was synthesized in accordance with the procedures described in Example 1. The support contained 78 microequivalents/gram of the nucleoside primer as determined by dimethoxytrityl release. Dry resin (350 mg) was packed into a column measuring 6 mm x 30 mm. The column was fitted into a BIO LOGICALS DNA/RNA synthesizer which was modified such that all steps were programmable. Nucleosides were added sequentially using a modified version of the standard phosphomonochloridite chemistry (Matteucci, M. D. and Caruthers, M. H., Tetrahedron Letters 21: 719–722 [1980]). Modifications to this standard procedure included: 1) capping unreacted 5' hydroxyl groups with a mixture of 5% N,N-dimethylaminopyridine, 17.5% acetic anhydride, 28.2% tetrahydrofuran and 49.3% 2,6-lutidine; and 2) removing the dimethoxytrityl groups with 4% dichloroacetic acid in chloroform.

Using this modified procedure, 400 micromoles of a 30 mM solution of the appropriate phosphomonochlorodite were reacted with the support for each nucleotide addition. The sequence synthesized was polymethacrylateprimer-3'd(TTTTGAAATAGGTA)5'. Once the oligonucleotide synthesis had been completed, the base blocking groups were removed by reacting the support bound DNA with concentrated ammonium hydroxide for 8–18 hours at 50° C. After extensive washing with water and 1M sodium chloride, the resin was dried and the terminal dimethoxytrityl groups were quantitated at 2.3 micromoles of bound oligonucleotide per gram of resin.

In order to evaluate the usefulness of the affinity hybridization support, two sequences of DNA were synthesized using identical phosphite chemistry. However, the standard base cleavable silica support was used (Matteucci, M. D. and Caruthers, M. H., Tetrahedron Letters 21:719–722 [1980]). One of these sequences was a 14 mer which was complementary to the affinity hybridization support, i.e., 5'-d(AAACTTTATCCATC) 3'. The other sequence was a 17 mer which was not complementary to the affinity hybridization support, i.e., 5'-d(GGAATATTCCCCCAGGC)3'. Both of these DNA sequences were labeled with $^{32}$p-ATP at the 5' end by standard procedures and purified on a polyacrylamide gel (Richardson, C. C., Proc. Nat'l. Acad. Sci., 54:158 [1965] and Maxam, A. and Gilbert, W., Methods of Enzymology, 65:449 [1979]).

The 14 mer and 17 mer sequences were tested for their ability to hybridize with the affinity support. This was done by incubating the DNA sequences with the affinity support for two hours at 25° C. in the presence of a buffer consisting of 1M sodium chloride, 10 mM Tris buffer, and 1 mM EDTA at a pH of 7.6. Sequences which did not hybridize were washed away with fifteen one-half ml aliquots of the buffer just described. The hybridized oligonucleotide sequences were then eluted with water.

In evaluating this comparative procedure, 30% of the 14 mer sequence and less than 5% of the 17 mer sequence were found to bind to the affinity column.

The new and improved polymeric support system for the synthesis of oligonucleotides, in accordance with the present invention, satisfies a long existing need in the art for a versatile polymeric support system that permits a convenient and quantitative release of all synthesized oligomers from a single type of polymeric support while maintaining a tolerance to mildly acidic and mildly basic reaction conditions.

It will be apparent from the foregoing that, while particular forms of the invention have been illustrated and described, various modifications can be made without departing from the spirit and scope of the invention. Accordingly, it is not intended that the invention be limited except as by the appended claims.

I claim:

1. A compound consisting essentially of a polymeric support and a primer, said compound having the structure:

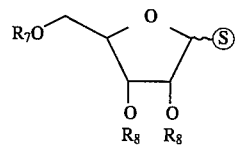

wherein Ⓢ is a solid support;

⁓ is a spacer of 1 to 50 atoms which is not cleaved under deprotecting conditions of oligonucleotide synthesis and is attached to said polymeric support;

$R_8$ is a protecting group on an oxidizable substituent; and $R_7$ is a protecting group for —OH.

2. A compound consisting essentially of a polymeric support and a primer, said compound having the structure:

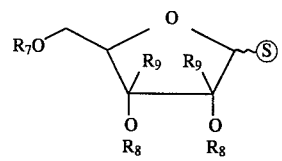

wherein Ⓢ is a solid support,

⁓ is a spacer of 1 to 50 atoms which is not cleaved under deprotecting conditions of oligonucleotide synthesis;

$R_8$ is a protecting group on an oxidizable substituent;

$R_7$ is a protecting group for OH; and $R_9$ are independently selected from the group consisting of H, alkyl, alkoxy and aryl.

* * * * *